United States Patent [19]

Kollias et al.

[11] Patent Number: 5,456,260
[45] Date of Patent: Oct. 10, 1995

[54] FLUORESCENCE DETECTION OF CELL PROLIFERATION

[75] Inventors: Nikiforos Kollias, Belmont; Robert Gillies, Cambridge; R. Rox Anderson, Lexington, all of Mass.

[73] Assignee: The General Hospital Corporation, Boston, Mass.

[21] Appl. No.: 223,428

[22] Filed: Apr. 5, 1994

[51] Int. Cl.[6] .................................................. A61B 6/00
[52] U.S. Cl. ................................................... 128/665
[58] Field of Search ................................... 128/633–635, 128/665, 664; 606/3, 13, 15–16

[56] References Cited

U.S. PATENT DOCUMENTS

| | | |
|---|---|---|
| 4,479,499 | 10/1984 | Alfano . |
| 4,930,516 | 6/1990 | Alfano et al. . |
| 4,957,114 | 9/1990 | Zeng et al. ........................ 606/3 X |
| 4,981,138 | 1/1991 | Deckelbaum et al. . |
| 5,131,398 | 7/1992 | Alfano et al. . |
| 5,205,291 | 4/1993 | Potter ........................... 128/665 X |
| 5,345,941 | 9/1994 | Rava et al. ......................... 128/665 |
| 5,348,018 | 9/1994 | Alfano et al. ...................... 128/665 |

OTHER PUBLICATIONS

Tang et al. "Pulsed and cw laser fluorescence spectra from cancerous, normal, and chemically treated normal human breast and lung tissues," Applied Optics, 28:2337–2342, 1989.

Primary Examiner—Angela D. Sykes
Attorney, Agent, or Firm—Fish & Richardson

[57] ABSTRACT

The method of the present invention is directed at detecting non-invasively and in vivo the rate of proliferation of epithelial cells in a human patient. The method is based on determining the optical spectra, preferably the fluorescence excitation spectra, from affected and non-affected areas of epithelial cells, and then comparing the two spectra from these regions. In particular, applicants have discovered that when human or animal skin is irradiated with light centered near 295 nm, fluorescence having a distinct maximum near 360 nm is induced.

17 Claims, 3 Drawing Sheets

FLUORESCENCE DETECTION OF CELL PROLIFERATION

This invention was made with Government support under Contract N00014-91-C-0084 awarded by the Department of the Navy. The Government has certain rights in the invention.

FIELD OF THE INVENTION

This invention relates to detection of rapidly proliferating cells.

BACKGROUND OF THE INVENTION

Epithelial cells form coherent cell sheets called epithelia, which line the inner and outer surfaces of the body. Absorptive epithelial cells, such as those lining the intestine and urogenital tract, are bound together by junctions that give the epithelia sheet mechanical strength and also make it impermeable to small molecules. Typically, the epithelia forms a membraneous cell cover that serves to protect and cover other organs, and produces secretions and excretions, and is used in assimilation.

Rapid proliferation of epithelial cells is often the result of a mutation occurring in a group of founder cells, which can then replicate and divide at faster rates than non-mutated cells. Mutated clones of epithelial cells which proliferate and spread rapidly can form cancers, or malignant tumors, which grow at the expense of non-affected cells and ultimately destroy neighboring tissue. In contrast to tumors which are cancerous, benign tumors proliferate to excess, but do not disseminate through the body via the lymphatic or circulatory systems, and can often be easily treated.

However, rapid proliferation of epithelial cells does not always lead to formation of tumors. For instance, proliferative skin diseases, such as psoriasis, eczema, mycosis fungoides, and lichen planus, result in rapid sloughing off of the stratum corneum without forming either malignant or benign tumorous growths. Endometriosis is characterized by rapidly proliferating epithelial cells, although no tumors are formed. In addition, a decrease in the proliferation of epithelial cells, often resulting in the retardation of wound healing, can be indicative of diseased tissue, or excess use of steroids.

Optical methods involving excitation of tissue with light resonant with electronic transitions in epithelial cells are used to monitor several cell properties. These methods are potentially valuable because optical radiation can be easily delivered to tissue using fiber optic devices, and sensitive detection devices can be used to measure small signals, such as fluorescence and absorption, from cells.

In Alfano et al., U.S. Pat. No. 5,131,398, an optical method is disclosed which is said to be useful for distinguishing cancerous tissue from benign tumor tissue. This method uses the optical excitation of tissue with light centered at 300 nm, followed by detection of fluorescence. The ratio of the induced fluorescence at two different frequencies is then used to determine the presence and nature of the tumor.

SUMMARY OF THE INVENTION

In general, the invention features a method of detecting abnormal epithelial cell proliferation, e.g., in a patient such as an animal or a human, by (a) sequentially exposing the epithelial cell to a set of at least two different wavelengths of incident ultra-violet radiation that induce the epithelial cell to sequentially emit at least two different fluorescence patterns, (b) measuring and recording the intensities of each of the different patterns at a first fluorescence emission wavelength to generate a test intensity profile, (c) obtaining a normal fluorescence emission intensity profile for normal epithelial cell proliferation for the first emission wavelength, and comparing the test profile with the normal profile, any difference between the profiles indicating abnormal proliferation of the epithelial cell.

As an additional set of steps, e.g., to increase sensitivity of the method, the invention also features, (d) sequentially re-exposing the epithelial cell to the set of incident ultra-violet radiation wavelengths, (e) measuring and recording the intensities of each of the different patterns at a second emission wavelength to generate a second test intensity profile, (f) obtaining a second normal fluorescence emission intensity profile for normal epithelial cell proliferation for the second emission wavelength, and comparing the second test profile with the second normal profile, any differences between the first profiles or the second profiles indicating abnormal proliferation of the epithelial cell.

In specific embodiments, the set of incident wavelengths includes wavelengths between 260 and 330 nm, or specifically includes a wavelength of about 295 nm. In specific embodiments, the fluorescence emission wavelength can be between 330 and 800 nm, or is at or about 360 nm.

The method covers abnormal proliferation that is either faster or slower than normal proliferation, and epithelial cells such as skin cells, e.g., basal or squamous skin cells, or epithelial cells of the gastrointestinal tract.

The detected abnormal proliferation can be an indication of dysplasia, hyperplasia, psoriasis, cancer, or wound healing. In each case, at least a doubling of the fluorescence intensity compared to that of a normal cell is an indication of abnormally fast proliferation. A five-fold or ten-fold increase is a certain sign of abnormally fast proliferation. Likewise, a lower intensity is an indication of slower than normal proliferation.

In another embodiment, the method is carried out at a starting point and an ending point of a period of time on the same epithelial cell to obtain a measurement of any variation of abnormal proliferation over said time period.

In addition, the normal fluorescence emission intensity profile is obtained by carrying out the method steps on a normally proliferating epithelial cell.

DESCRIPTION OF THE PREFERRED EMBODIMENTS

The method of the present invention is directed at detecting non-invasively and in vivo the rate of proliferation of epithelial cells in a human patient. The method is based on determining the optical spectra, preferably the fluorescence excitation spectra, from affected and non-affected areas of epithelial cells, and then comparing the two spectra from these regions. In particular, applicants have discovered that when human or animal skin is irradiated with light centered near 295 nm, fluorescence having a distinct maximum near 360 nm is induced.

Applicants have determined that the magnitude of the fluorescence at 360 nm can be made to increase significantly by the proliferation or hyperproliferation of epidermal cells, which can be induced by an increase in cell turnover rate. This effect can be modeled by removing layers of the stratum corneum using adhesive tape or scraping the stratum corneum, thus increasing the epidermal cell turnover rate and increasing the epithelial cell proliferation rate in a patient.

Using the apparatus of the present invention, it is possible to induce and measure fluorescence in affected (i.e., cells undergoing rapid proliferation) and non-affected (i.e., normal cells) regions. Following spectroscopic measurement, the optical properties of affected and non-affected cells can be correlated to their degree of proliferation.

Optical Apparatus

Figure 1:
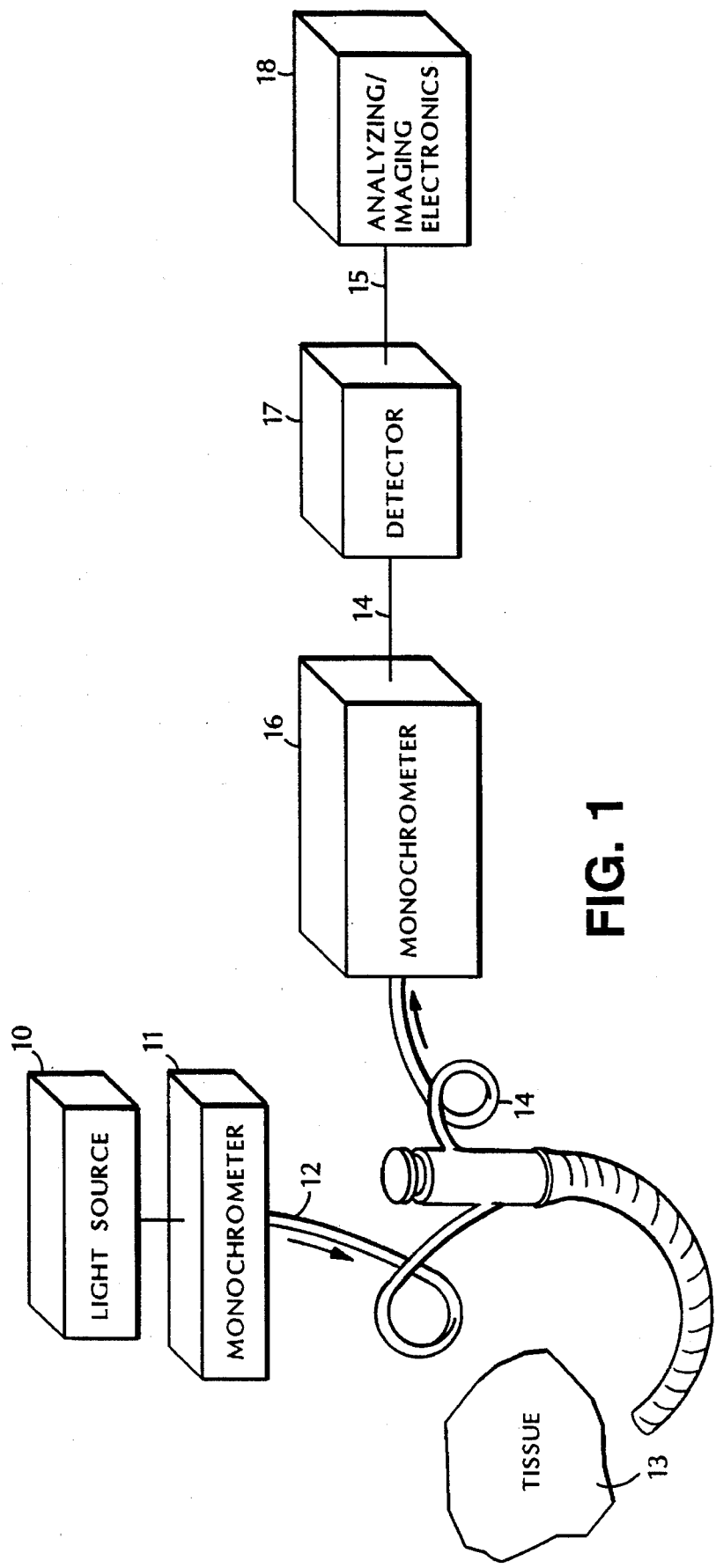
FIG. 1 is a drawing of the apparatus of the invention.

Referring now to FIG. 1, the optical apparatus used to induce and measure tissue fluorescence has a light source 10 connected to a monochromator 11 using a fiber optic bundle 12. Preferably, the light source is broad band, and is capable of emitting optical frequencies in the ultraviolet (UV) and near UV frequency range (200–450 nm). In preferred embodiments, a white light source is used. Alternatively, a tunable laser capable of emitting UV frequencies, such as an excimer laser, can be used.

A first monochromator 11 is used to filter optical frequencies from the broad band light source, and preferably has a band width on the order of 0.5–1 nm. Following propagation through the monochromator, optical radiation is delivered to the tissue sample 13 using fiber optic bundle 14. Preferably, quartz fibers which do not have significant absorption in the UV, and therefore do not attenuate the propagating light, are used as the fiber optic material. The quartz fibers are not in contact with the tissue sample. The narrow band incident optical radiation is delivered to the tissue sample, where it is absorbed by the cells of tissue sample 13 and used to induce fluorescence.

Portions of the emitted light are collected by a second fiber optic bundle 15, which separates from the fiber used to deliver the excitation field to the tissue. Fiber optic bundle 15 is interfaced to a second monochromator 16 having a bandwidth between 0.5 and 1 nm, which can be scanned or set at a particular wavelength. For the fluorescence excitation measurements, the second monochromator 16 is set at a wavelength (e.g., 360 nm) while the first monochromator 11 is scanned from approximately 250 to 450 nm. Intensity of the fluorescence at the wavelength determined by the second monochromator 16 is measured as a function of excitation wavelength.

In order detect low levels of emitted radiation, photon counting photomultiplier tubes, in conjunction with photon counting electronics, may be used in the method of the present invention. Alternatively, the excitation field can be modulated at a fixed frequency, allowing the emitted field to be measured with a photodetector and lock-in amplifier using techniques known in the art.

Alternatively, it is possible to fix the exciting optical field at a particular wavelength with the first monochromator 11, and scan the second monochromator in order to measure the emission spectrum of the sample 13. In this embodiment, it is possible to interface a CCD detector or diode array to the second monochromator 16 in order to detect the entire spectrum at once. In all the above-identified embodiments, analysis of spectral data is preferably performed using a computer.

Optical Measurement of Normal and Rapidly Proliferating Epithelial Cells

Using fluorescence excitation spectra taken from the skin of 6–12 week old mice and human volunteers having normal and rapidly proliferating psoriatic skin, various bands in the fluorescence excitation spectra were assigned to optical transitions occurring in specific chemical species. In particular, the human skin inflamed following mechanical abrasions displayed an increase in the fluorescence intensity at 360 nm when the excitation wavelength was between 270–275 nanometers, indicating that this particular band is correlated with rapid proliferation of skin. In addition, in nearly all skin samples, an excitation wavelength of 295 nm resulted in a dramatic increase in the fluorescence intensity at 360 nm. This feature is associated with fluorescence of tryptophan, and is associated with cells other than skin cells. Other epithelial cells, such as pancreatic cells, cells associated with endometriosis, cells lining the intestinal tract, and other cells which form membraneous linings around tissue, are expected to demonstrate similar optical behavior. The dramatic Stokes shift of 65 nm (i.e., the difference in wavelength between emission maxima and excitation maxima wavelengths) appears to correspond to the optical response of epithelial cells in general.

Figure 2:
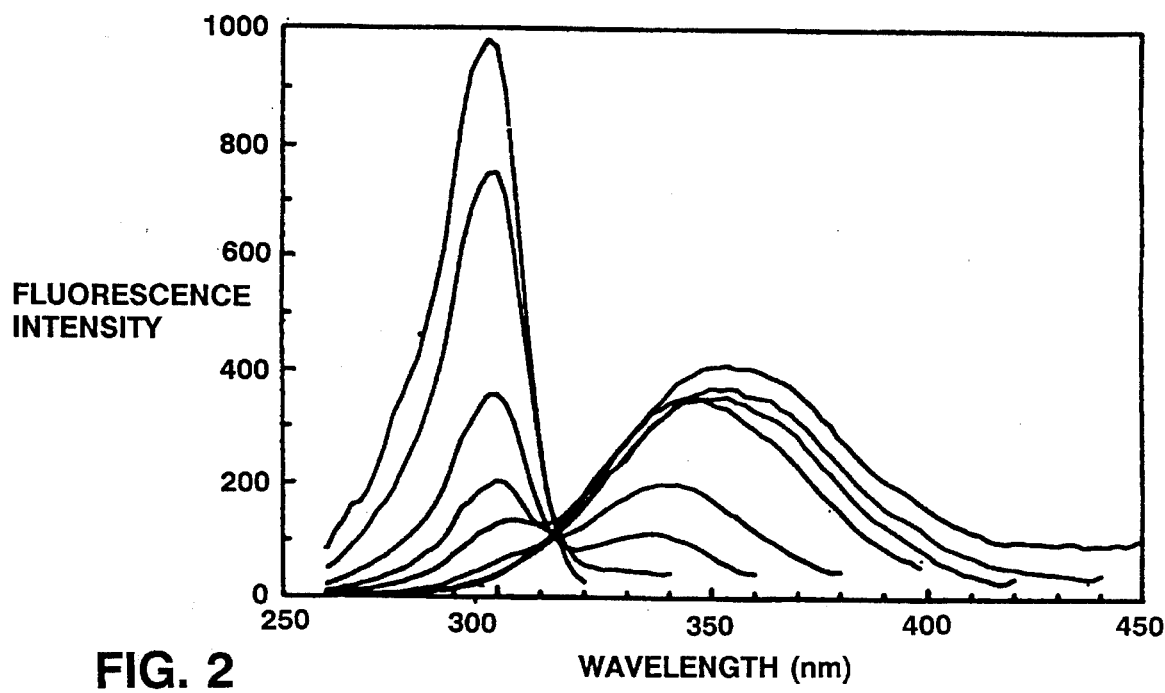
FIG. 2 is a graph showing a fluorescence excitation spectrum taken using the method of the invention.

Referring now to FIG. 2, the fluorescence excitation spectra taken from the skin of 6 weeks old mice indicates the substantial difference in the spectra taken when the monochromator filtering the emission (the "emission monochromator") is set at different wavelengths in the UV and near UV frequency ranges. The spectrum peaked at 295 nm (i.e., the excitation frequency is 295 nm) corresponds to an emission monochromator setting of 360 nm. As the emission monochromator is moved in 20 nm intervals to higher wavelength settings, the peak at 295 nm is rapidly decreased, indicating that absorption into the band assigned to tryptophan results in a Stokes-shifted fluorescence peak at 360 nm.

The magnitude of the fluorescence peak at 360 nm, following optical excitation at 295 nm, can be made to increase significantly by experimental induction of hyperproliferation of the epidermal cells. This technique is used to model proliferation in skin cells. It is well known that epidermal cells (keratinocytes) respond to insults that damage the epidermis by increasing their turnover rate. The optical properties of normal and rapidly proliferating skin can therefore be modeled by producing minor injuries to skin using mechanical abrasion or removal of stratum corneum layers with adhesive tape, and then measuring the time dependence of the fluorescence behavior of the recovering skin. Changes in signal in the emission intensity at 360 nm, following excitation at 295 nm, were observed 3–7 days after inducing the proliferation in the skin of normal human volunteers. The magnitudes of the peaks at 295 nm decreased by factors of 6–10 as the damaged skin samples were allowed to heal.

Optical Measurement of Psoriatic Skin and Basal Skin Cell Cancer

Figure 3:
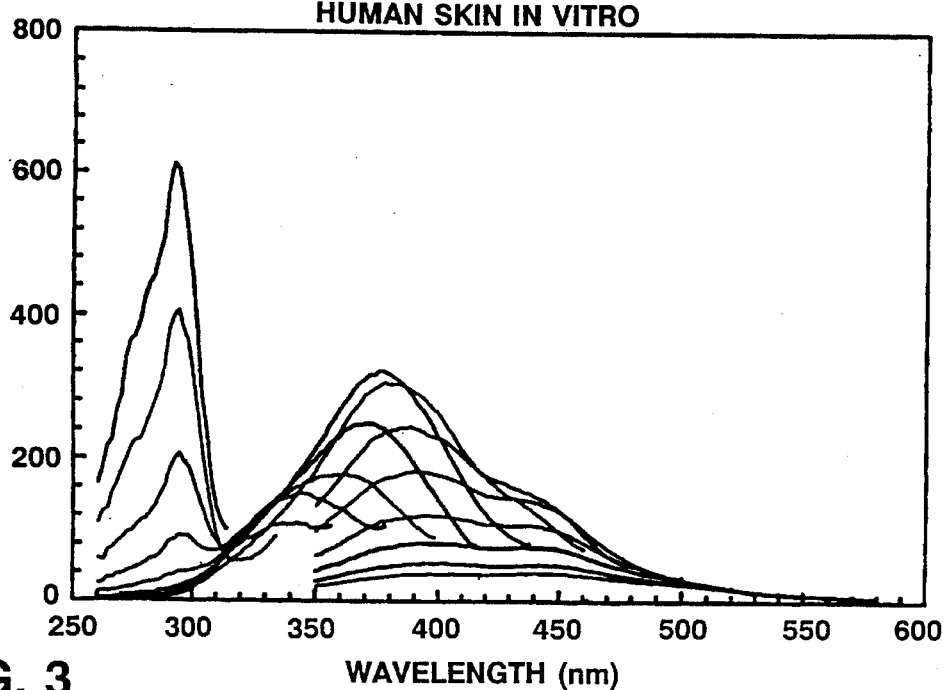
FIG. 3 is a graph showing a fluorescence excitation spectrum taken from human skin in vivo.
Figure 4:
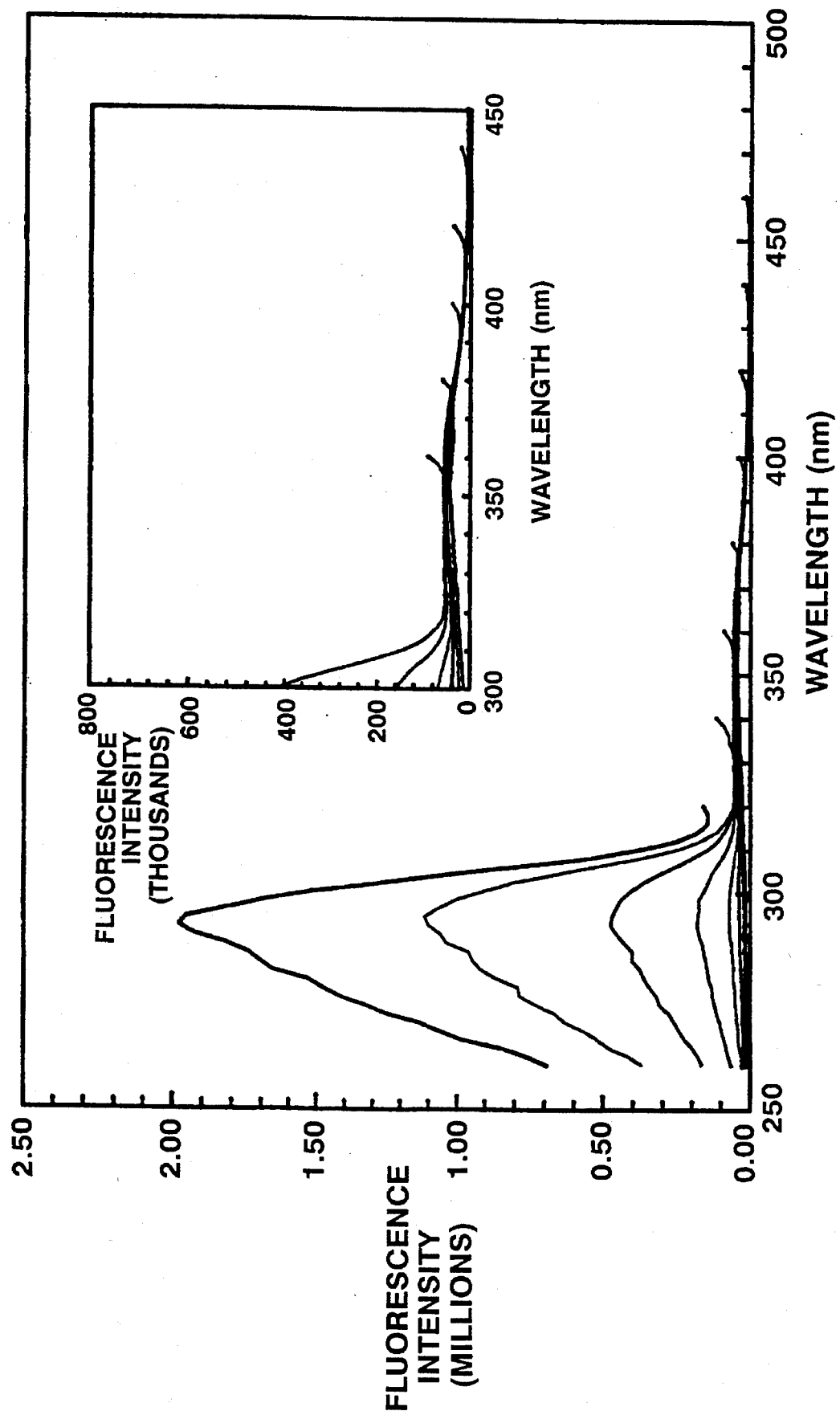
FIG. 4 is a graph showing a fluorescence excitation spectrum taken from psoriatic skin using the method of the invention.

Fluorescence excitation spectra was also used to measure the optical properties of psoratic skin in human patients. Referring now to FIG. 3, the fluorescence excitation spectra taken from normal human skin displayed features similar to those observed in FIG. 2. In particular, when 295 nm is used as the excitation wavelength, the emission is peaked at 360 nm. As the monochromator filtering the fluorescence is moved to higher wavelengths, the peak in the data at 295 nm is decreased, indicating a Stokes shift of 65 nm. In addition, the width of the peak centered around 295 nm is indicative of the absorptive behavior of normal human skin. This data can be compared to fluorescence excitation spectra taken from psoratic skin of human patients. Referring now to FIG. 4, a 65 nm Stokes shift is evident in the data, with the width of the peak centered around 295 nm being significantly broader than the data taken from normal human skin. A shoulder extending to 260 nm which is correlated directly to the presence of psoriatic skin is evident in the data when the emission monochromator is centered between 360 to approximately 400 nm. This spectral feature can be used to distinguish rapidly proliferating skin cells from normal skin cells using a fast, non-invasive, in vivo diagnostic method.

Additional measurements were performed on human patients having lesions of basal skin cell cancer. Fluorescence excitation spectra indicate that data taken from affected skin have similar spectral features as the data shown in FIG. 3, with the intensity of the peak near 295 nm increased by a factor of approximately 10 compared to data taken from normal skin samples. The descrepancy in optical properties of normal and cancerous skin cells indicate the ability of the method of the present invention to measure non-invasively the characteristics of rapidly proliferating epithelial cells, including cancerous skin cells.

In addition, the method of the present invention may be used to detect squamous cell carcinomas, malignant melanoma, and other types of cell proliferation associated with carcinoma in situ. Other uses associated with detection of affected epithelial cells, such as measurement of precancerous lesions which involve hyperproliferation, as in dysplasia and hyperplasia, the monitoring and detection of wound healing, monitoring decreases in cell proliferation, and general uses in dermatology, are also within the scope of the method of the present invention. Furthermore, optical methods which measure rapid proliferation of the skin necessarily measure the proliferation of the dermis and epidermis, which contains live cells, as opposed to the stratum corneum. Therefore, characteristics of these skin layers, particularly biological processes occurring at the interface between the epidermis and dermis, can be measured with the method of the present invention.

Methods of Use

The strong optical absorption in affected and non-affected skin cells at 295 nm, in conjunction with the magnitude of the induced emission at 360 nm, indicates the ability of the method of the present invention, using these combined wavelengths, to make sensitive measurements of rapidly proliferating skin. This is crucial when UV wavelengths, particularly those peaked near 295 nm, are used. Light in this spectral region is known to cause cancer, and it necessary to minimize exposure in patients. Using the method of the present invention, optical fluences between 0.05 and 1.0 $mW/cm^2$ can be used to detect the rapid proliferation of epithelial cells. Skin cancer, erythema, and other skin afflictions related to incident UV radiation are unlikely to occur using optical fluences in this range, which are well below the threshold level required to elicit clinically observable biological responses.

Because optical excitation and emission fields can be delivered to and collected from tissue with optical fibers, it is also possible to measure optical properties of epithelial cells of internal organs using an insertion catheter or similar device.

In addition, the method of the present invention may also be used to make in vitro measurements of proliferating epithelial cells, such as measurements relating to cell division in culture dishes.

The foregoing descriptions of preferred embodiments of the method and apparatus of the present invention have been presented for purposes of illustration and description. They are not intended to be exhaustive or to limit the invention to the precise form disclosed. The embodiments chosen are described in order to best explain the principles of the invention.

What is claimed is:

1. A method of detecting abnormal epithelial cell proliferation by monitoring tryptophan emission from the cell, said method comprising the steps of:

(a) sequentially exposing the epithelial cell to a set of at least two different wavelengths of incident ultra-violet radiation that induce tryptophan present in the epithelial cell to sequentially emit at least two different emission patterns, (b) measuring and recording the intensities of each of said different emission patterns at an emission wavelength corresponding substantially to the maximum emission wavelength of tryptophan to generate a test intensity profile, (c) obtaining a normal emission intensity profile for tryptophan present in a normally proliferating epithelial cell, and comparing said test profile with said normal profile near the maximum tryptophan emission wavelength, with any difference in emission near said maximum tryptophan emission wavelength of the test profile indicating abnormal proliferation of the epithelial cell.

2. The method of claim 1, further comprising the steps of:

(d) sequentially re-exposing the epithelial cell to said set of incident ultra-violet radiation wavelengths, (e) measuring and recording the intensities of each of said different patterns at an emission wavelength other than the maximum tryptophan emission wavelength to generate a second test intensity profile, (f) obtaining a second normal fluorescence emission intensity profile for normal epithelial cell proliferation for said emission wavelength other than the maximum tryptophan emission wavelength, and comparing said second test profile with said second normal profile, any differences between said first profiles or said second profiles indicating abnormal proliferation of the epithelial cell.

3. A method of detecting abnormal epithelial cell proliferation by monitoring tryptophan emission from the cell, said method comprising the steps of:

(a) exposing the epithelial cell to incident ultraviolet wavelengths in order to induce tryptophan present in the epithelial cell to emit an emission pattern, (b) measuring and recording the intensity of the emission pattern of tryptophan to generate a test intensity profile, (c) obtaining a normal emission intensity profile for tryptophan present in a normally proliferating epithelial cell, and comparing said test profile with said normal profile at a wavelength corresponding substantially to the maximum emission wavelength of tryptophan, with any difference in emission of the test profile relative to the normal profile near the maximum emission wavelength of tryptophan indicating abnormal proliferation of the epithelial cell.

4. The method of claim 1 or 3, wherein said set of incident wavelengths includes wavelengths between 260 and 330 nm.

5. The method of claim 3, wherein said set of wavelengths includes a wavelength of about 295 nm.

6. The method of claim 1 or 3, wherein said emission wavelength is between 330 and 800 nm.

7. The method of claim 6, wherein said emission wavelength is about 360 nm.

8. The method of claim 1 or 3, wherein said abnormal proliferation is faster than normal proliferation.

9. The method of claim 8, wherein said faster proliferation is an indication of cancer.

10. The method of claim 8, wherein said faster proliferation is an indication of wound healing.

11. The method of claim 1 or 3, wherein said abnormal proliferation is slower than normal proliferation.

12. The method of claim 1 or 3, wherein said epithelial cell is a skin cell.

13. The method of claim 12, wherein said faster proliferation is an indication of psoriasis.

14. The method of claim 1 or 3, wherein said epithelial cell is in a patient.

15. The method of claim 14, wherein said patient is a human.

16. The method of claim 1 or 3, wherein said method is carried out at a starting point and an ending point of a period of time on the same epithelial cell to obtain a measurement of any variation of abnormal proliferation over said time period.

17. The method of claim 1 or 3, wherein said normal fluorescence emission intensity profile is obtained by carrying out the method of claim 1 on a normally proliferating epithelial cell.

* * * * *